(12) United States Patent
Hamada et al.

(10) Patent No.: US 9,539,057 B2
(45) Date of Patent: Jan. 10, 2017

(54) LASER IRRADIATION TIP, LASER IRRADIATION HANDPIECE, LASER TREATMENT APPARATUS, AND LASER IRRADIATION TIP END MEMBER

(71) Applicant: J. Morita Manufacturing Corporation, Kyoto (JP)

(72) Inventors: Kazunori Hamada, Kyoto (JP); Mikinori Nishimura, Kyoto (JP); Masaki Odaka, Kyoto (JP); Tetsuzo Ito, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 753 days.

(21) Appl. No.: 13/870,435

(22) Filed: Apr. 25, 2013

(65) Prior Publication Data
US 2013/0289548 A1    Oct. 31, 2013

(30) Foreign Application Priority Data
Apr. 26, 2012 (JP) ................. 2012-100738

(51) Int. Cl.
*A61B 18/18*    (2006.01)
*A61B 1/04*     (2006.01)
(Continued)

(52) U.S. Cl.
CPC .......... *A61B 18/22* (2013.01); *A61C 1/0046* (2013.01); *A61B 2018/00166* (2013.01);
(Continued)

(58) Field of Classification Search
CPC .............. A61B 17/1604; A61B 17/00234; A61B 17/1655; A61B 1/00045; A61B 1/00135; A61B 1/015; A61B 1/04; A61B 1/06; A61B 19/5244
(Continued)

(56) References Cited

U.S. PATENT DOCUMENTS 4,330,279 A   5/1982 Heil et al.
4,826,431 A   5/1989 Fujimura et al.
(Continued)

FOREIGN PATENT DOCUMENTS

JP   07-051287 A   2/1995
JP   08-154952 A   6/1996
(Continued)

OTHER PUBLICATIONS

Patent Abstracts of Japan, Publication No. 07-051287, Published on Feb. 28, 1995, 1 page.
(Continued)

*Primary Examiner* — John P Leubecker
*Assistant Examiner* — William Chou
(74) *Attorney, Agent, or Firm* — Osha Liang LLP

(57) ABSTRACT

A laser irradiation tip has a main body and a tip end portion. The main body is connected with a handpiece and irradiating therapeutic laser with high absorbability in water. The tip end portion being connected with the main body. The main body of the laser irradiation tip has an optical fiber for guiding the therapeutic laser, a water flow path, and an air flow path in a parallel manner. The tip end portion of the laser irradiation tip has a connection portion with the main body, a water guide path communicated with the water flow path of the main body, an air guide path communicated with the air flow path of the main body, a fiber guide portion capable of inserting a tip side portion of the optical fiber, and a mixing chamber of water and air.

12 Claims, 5 Drawing Sheets

(51) Int. Cl.
*A61B 1/12* (2006.01)
*A61B 18/22* (2006.01)
*A61C 1/00* (2006.01)
*A61B 18/00* (2006.01)
*A61C 1/05* (2006.01)

(52) U.S. Cl.
CPC ............ *A61B 2018/00321* (2013.01); *A61B 2018/00601* (2013.01); *A61C 1/052* (2013.01)

(58) Field of Classification Search
USPC ....... 600/424; 606/2, 13, 15, 16, 17; 604/21; 607/89; 433/29
See application file for complete search history.

(56) References Cited

U.S. PATENT DOCUMENTS

| | | | |
|---|---|---|---|
| 5,199,870 A | 4/1993 | Steiner et al. | |
| 5,300,067 A * | 4/1994 | Nakajima | A61B 17/36 606/16 |
| 6,083,218 A | 7/2000 | Chou | |
| 6,354,519 B1 * | 3/2002 | Kidooka | A61B 1/126 239/463 |
| 6,438,305 B1 * | 8/2002 | Kataoka et al. | G02B 6/02 385/125 |
| 9,211,059 B2 * | 12/2015 | Drach | A61B 17/3474 |
| 2008/0188715 A1 * | 8/2008 | Fujimoto | A61B 1/00091 600/157 |
| 2009/0030438 A1 * | 1/2009 | Stulen | A61B 17/32 606/169 |

FOREIGN PATENT DOCUMENTS

| | | |
|---|---|---|
| JP | 10-057400 A | 3/1998 |
| JP | 2001-000442 A | 1/2001 |
| JP | 2010-046474 A | 3/2010 |
| WO | 90/11728 A1 | 10/1990 |

OTHER PUBLICATIONS

Patent Abstracts of Japan, Publication No. 08-154952, Published on Jun. 18, 1996, 1 page.

* cited by examiner

LASER IRRADIATION TIP, LASER IRRADIATION HANDPIECE, LASER TREATMENT APPARATUS, AND LASER IRRADIATION TIP END MEMBER

TECHNICAL FIELD

The present invention relates to a laser irradiation tip, a laser irradiation handpiece having the laser irradiation tip, a laser treatment apparatus including the laser irradiation handpiece, and a laser irradiation tip end member constituting the laser irradiation tip. More particularly, the present invention relates to improvement of spray mechanism of a treatment device for irradiating laser during spraying of mixed mist of water and air.

BACKGROUND ART

Recently, a laser treatment apparatus has been widely used in the field of dental examination. The laser treatment apparatus basically comprises a laser generation apparatus, an optical guiding device for guiding laser beam, a handpiece connected with the tip end of the optical guiding device, and a laser irradiation tip mounted on the tip end of the handpiece. The laser generation apparatus of the laser treatment apparatus can use several kinds of laser generation apparatus for generating laser such as Er:YAG laser, carbon dioxide laser, Nd:YAG laser, semiconductor laser. Er:YAG laser with high absorbability in water has been used these days, wherein a spray mechanism is attached for spraying mixed mist of water and air on a laser irradiation region taking advantage of absorbability in water. The laser treatment apparatus having the spray mechanism of mixed mist of water and air is disclosed in Patent Literatures 1 to 4.

Patent Literature 1 discloses a dental treatment apparatus for removing matter from the surface of teeth by pulsed laser in which a liquid layer of 10 to 100 micrometers in thickness is formed on teeth. Patent Literature 2 discloses a laser treatment apparatus which is provided with a handpiece for irradiating Er:YAG laser and sprays mixed fluid of liquid and gas to a patient to be irradiated with laser from a position behind an output end of laser. Patent Literature 3 discloses a laser treatment apparatus which avoids extra laser absorption by setting timing of spraying mixed mist of water and air at the time of irradiating laser pulse. The paragraph [0004] in Patent Literature 4 discloses an optical cutter (laser treatment apparatus) for irradiating Nd:YAG laser on an affected area in which water and air are mixed in a mixing chamber provided around a fiber conduit pipe for laser irradiation and delivered along the conduit pipe via a mesh screen. Patent Literature 4 discloses that a program is provided for adjusting size and speed of liquid particles in such a manner that electromagnetic energy is absorbed by damp air and/or atomized fluid particles to impart disruptive forces to skin (referring to FIG. 5).

Patent Literature 5 discloses an apparatus for removing dental caries by laser having a delivery device for supplying cooling water to an irradiation area with laser, not for spraying mixed mist of water and air.

CITATION LIST

Patent Literature
PTL 1: WO90/11728
PTL 2: Japanese Patent Publication (not examined) H07-51287
PTL 3: Japanese Patent Publication (not examined) H08-154952
PTL 4: Japanese Patent Publication (not examined) 2001-442
PTL 5: Japanese Patent Publication (not examined) H10-57400

SUMMARY OF INVENTION

Technical Problem

The dental treatment apparatus disclosed in PTL 1 is designed to enhance cutting efficiency by forming a thin water film on the surface of teeth when pulse laser is irradiated; however, it does not disclose specific methods and configuration for forming the water film.

PTL 2 discloses the hourly supply amount of liquid and gas of the mixed fluid of liquid and gas per minute; however it is unclear whether the mixed fluid is in the form of mist. In fact, there is a worry that mist has a large particle diameter and is absorbed in water before laser reaches an object to be cut.

In PTL 3, irradiation of laser and stop of spray are required to be well timed and such a control is anticipated to be difficult. Irradiation pulse frequency of therapeutic laser is 1 to 30 pps (pulse per second), so that it is extremely difficult to timely stop spraying in accordance with the frequency. In case that they are timed, it is clear that, in view of speed of laser, laser irradiation catches up with spray soon and laser is absorbed in water after all.

In the paragraph [0004] in PTL 4, a mesh screen is provided for the mixing chamber for passing the mixture, thereby increasing the number of members unavoidably. A wall can be provided on the outer side of the chamber of the mesh screen and the mixture of water and air can be sprayed from a narrow discharge port around a fiber conduit pipe. Therefore, there is a fear that the spray direction of the mixture may not be fixed and laser may hardly reach the object to be cut. In addition, a complicated apparatus is required in order to program the size and speed of particles, thereby the apparatus becomes expensive and large scale.

PTL 5 discloses a system for supplying cooling water as mentioned above but not for spraying mixed mist of water and air. Therefore, an apparatus for sucking water supplied to an affected area is required so that operation becomes complicated in addition to increase in size and cost of the apparatus. Specifically in dental examination, while a dentist holds a laser handpiece with his dominant hand, the dentist holds patients' lips with the other hand for obtaining wide eyesight and operative field, or he observes by reflecting an area, which is difficult to be perceived, with a dental mirror in the other hand. When a suction mechanism (a vacuum handpiece) is further required to be handled, he needs help of an assistant for sucking and removing cut objects, secretion, and so on. In addition, the patients further suffer from insertion of a plurality of handpieces in mouth.

The present invention is proposed in view of the above-mentioned problems. The object of the present invention is to provide a laser irradiation tip, a laser irradiation handpiece, a laser treatment apparatus and a laser irradiation tip end member in which mixed mist of water and air is extremely minute, and a thin water film is formed on an object to be cut, thereby achieving more efficient cutting ability.

Solution to Problem

The laser irradiation tip of the present invention has a main body and a tip end portion, the main body being connected with a handpiece and irradiating therapeutic laser with high absorbability in water, and the tip end portion being connected with the main body. The main body of the laser irradiation tip has an optical fiber for guiding the therapeutic laser, a water flow path, and an air flow path in a parallel manner. The tip end portion of the laser irradiation tip has a connection portion with the main body, a water guide path communicated with the water flow path of the main body, an air guide path communicated with the air flow path of the main body, a fiber guide portion capable of inserting a tip side portion of the optical fiber, and a mixing chamber of water and air. The optical fiber is inserted into the fiber guide portion so as to project from a front end surface of the tip end portion of the laser irradiation tip, the mixing chamber of water and air is formed by a concave portion which opens on the front end surface of the tip end portion and dents toward the main body side of the laser irradiation tip, tip end open portions of the water guide path and the air guide path face a bottom of the concave portion, and sectional area of the concave portion is larger than total area of the tip end opening portions. Water from the water guide path and air from the air guide path are mixed in the concave portion, and mixed mist of water and air is sprayed substantially parallel to the therapeutic laser in an irradiation direction of the therapeutic laser from a spray end at an opening of the concave portion.

The main body of the laser irradiation tip of the present invention can be constituted with a curved bar-shaped body. In addition, amount of water flowing in the water guide path can be 1.0 to 20.0 milliliter per minute and amount of air flowing in the air guide path can be 0.5 to 15.0 liter per minute. Depth of the concave portion from the spray end can be 0.5 to 1.5 mm. Furthermore, the tip end portion of the laser irradiation tip can be another member different from the main body of the laser irradiation tip, and the connection portion can be a mounting portion capable of attaching or removing the tip end portion to or from the main body.

The laser irradiation handpiece of the present invention is characterized in that a handpiece body capable of handling with fingers incorporates a laser beam guide path for guiding therapeutic laser with high absorbability in water, a water pipe line, and an air pipe line. The above-mentioned laser irradiation tip is attached to the handpiece body in such a manner that the optical fiber provided for the laser irradiation tip, the water flow path, and the air flow path are connected with the laser beam guide path, the water pipe line, and the air pipe line, respectively.

A laser treatment apparatus of the preset invention comprises a laser oscillator for oscillating therapeutic laser with high absorbability in water, a laser transmitter for transmitting the therapeutic laser, a water delivery circuit, an air delivery circuit, and the above mentioned laser irradiation handpiece. The laser irradiation tip end member of the present invention comprises a mounting portion capable of being attached to or removed from a main body of a laser irradiation tip having an optical fiber for guiding therapeutic laser with high absorbability in water, a water flow path, and an air flow path in a parallel manner. The laser irradiation tip end member further comprises a water guide path communicated with the water flow path, an air guide path communicated with the air flow path, a fiber guide portion capable of inserting a tip side portion of the optical fiber, and a mixing chamber of water and air. The optical fiber is inserted into the fiber guide portion so as to project from a front end portion thereof, the mixing chamber of water and air is formed by a concave portion which opens on a front end surface of the laser irradiation tip end member and dents toward the main body side, and tip end open portions of the water guide path and the air guide path face a bottom of the concave portion, and sectional area of the concave portion is larger than total area of the tip end open portions. Furthermore, water from the water guide path and air from the air guide path are mixed in the concave portion and mixed mist of water and air is sprayed substantially parallel to the therapeutic laser in an irradiation direction of the therapeutic laser from a spray end at the opening of the concave portion.

Advantageous Effects of Invention

In the laser irradiation tip, the laser irradiation handpiece, the laser treatment apparatus, and the laser irradiation tip end member of the present invention, the laser beam generated by the laser oscillator of the laser treatment apparatus reaches the laser irradiation tip mounted on the main body of the laser irradiation handpiece via the laser transmitter and the light guide path housed in the laser irradiation handpiece. The laser beam reached the laser irradiation tip is transmitted to the optical fiber provided on the main body of the laser irradiation tip, passes through the fiber guide portion at the tip end portion of the laser irradiation tip, and is irradiated on a target object from the tip end of the optical fiber projecting from the front end of the tip end portion of the laser irradiation tip. Water sent from the water delivery circuit of the laser treatment apparatus reaches the laser irradiation tip mounted on the main body of the laser irradiation handpiece via the water pipe line housed in the laser irradiation handpiece. The water reached the laser irradiation tip flows to the mixing chamber of water and air, to be mentioned later, via the water flow path of the main body of the laser irradiation tip and the water guide path at the tip end portion of the laser irradiation tip. Air sent from the air delivery circuit of the laser treatment apparatus reaches the laser irradiation tip mounted on the main body of the laser irradiation handpiece via the air pipe line housed in the laser irradiation handpiece. Air reached the laser irradiation tip flows to the mixing chamber of water and air, to be mentioned later, via the air flow path of the main body of the laser irradiation tip and the air guide path at the tip end portion of the laser irradiation tip.

The mixing chamber of water and air is formed by the concave portion which opens on the front end surface of the tip end portion of the laser irradiation tip (the tip end member) and dents toward the main body side of the laser irradiation tip, the tip openings of the water guide path and the air guide path face the bottom of the concave portion, thereby mixing water and air flowing from each tip opening in the concave portion. The sectional area of the concave portion is designed to be larger than total area of the tip openings, so that fluid pressure values of water and air flowing from the tip openings decrease in the concave portion. As a result, water particles are refined and mixed with air, thereby generating uniform mixed mist of water with minute particles and air (called mixed water/air mist, hereinafter). The mixed water/air mist is sprayed substantially parallel to therapeutic laser in the irradiation direction of the therapeutic laser from the spray end at the opening of the concave portion. Because the mixed water/air mist comprises uniform mist of minute water particles and, in addition, is sprayed substantially parallel to therapeutic laser, laser beam irradiated from the tip end of the optical fiber is avoided to be absorbed in the mist before reaching the object to be irradiated. If the object to be irradiated is an object to be cut, like teeth, cutting efficiency is improved with efficient reduction in laser output. The mixed water/air mist attaches on the surface of the object to be irradiated and forms a thin water film, so that energy of laser can be absorbed and distributed, thereby executing efficient transpiration (cutting). Furthermore, the sprayed mixed water/air mist does not form drops of water on the surface of the object to be irradiated, so that it is not necessary to suck and remove water drop, thereby reducing burden on an operator and pain of patients.

When the main body of the laser irradiation tip is constituted with the curved bar-shaped body, the affected area (teeth) is accessible without hindering eyesight of an operator by the handpiece in case of dental examination wherein handpieces are inserted in a narrow oral cavity.

When amount of water flowing in the water guide path of the main body of the laser irradiation tip is designed to be 1.0 to 20.0 milliliter per minute, amount of air flowing in the air guide path is designed to be 0.5 to 15.0 liter per minute, and depth of the concave portion constituting the mixing chamber is designed to be 0.5 to 1.5 mm from the spray end, most suitable spray condition of mixed water/air mist as mentioned above is able to be obtained. When amount of water is less than 1.0 milliliter per minute and amount of air is less than 0.5 liter per minute, water drops become too large and spray condition of mist is apt to be disturbed or pulsated. On the other hand, when amount of water is larger than 20.0 milliliter per minute and amount of air is larger than 15.0 liter per minute, water and air are not appropriately mixed, spray condition of mist is apt to be disturbed, the spray direction of the mist does not become substantially parallel to the therapeutic laser beam, and the spray direction is apt to incline. When depth of the concave portion is less than 0.5 mm, water and air are not well mixed. When the depth of the concave portion is larger than 1.5 mm, water and air are not appropriately mixed, water drops are apt to become larger, the spray condition of the mist does not become substantially parallel to the therapeutic laser beam and the spray direction is apt to incline.

When the tip end portion of the laser irradiation tip is another member different from the main body of the laser irradiation tip, and the connection portion is the mounting portion capable of attaching or removing the tip end portion to or from the main body, the above-mentioned spray function of mixed water/air mist is able to be attached later to an existing laser irradiation tip which is not capable of spraying the mixed water/air mist and the laser irradiation tip is able to be preferably applied in many examinations. When various kinds of laser tips are prepared, such as laser tips having concave portions of different size (sectional area, depth and so on) and the laser tips being different in diameter of the tip end openings of the water guide paths and air guide paths, laser treatment can be executed while spraying mixed water/air mist appropriate for the above-mentioned examination by choosing one of the above-mentioned laser tips. In addition, an operator has freedom for selection of handpiece and treatment methods.

DESCRIPTION OF EMBODIMENTS

Figure 1:
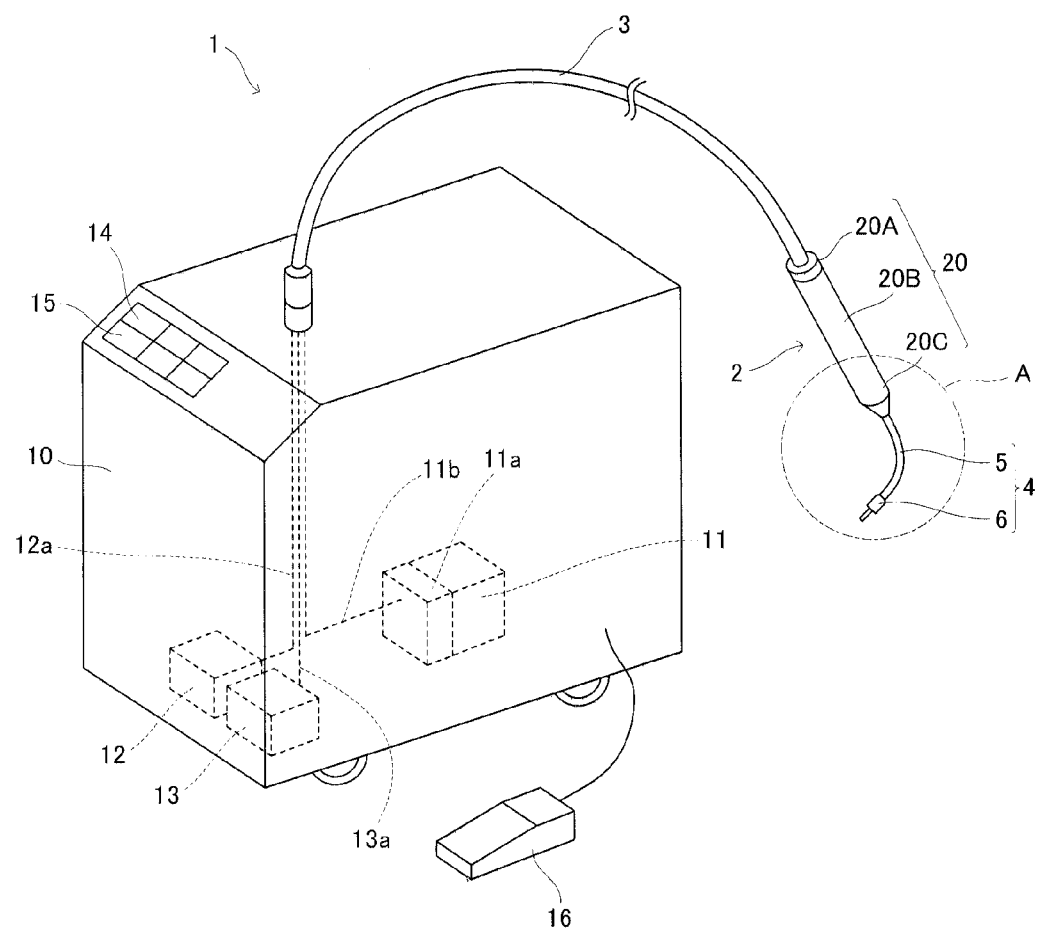
FIG. 1 is a diagrammatical entire view of the dental laser treatment apparatus in one embodiment of the laser treatment apparatus of the present invention.

Embodiments of the laser irradiation tip, the laser irradiation handpiece having the laser irradiation tip, the laser treatment apparatus, and the laser irradiation tip end member of the present invention are explained based on the drawings. A laser treatment apparatus 1 shown in FIG. 1 is a dental laser treatment apparatus in which a laser oscillator 11 oscillating laser with high absorbability in water, a water delivery circuit 12 supplying water (sometimes including normal saline) and an air delivery circuit 13 supplying air (sometimes including inert gas) are provided in a laser apparatus body 10 with casters. Laser generated by the laser oscillator 11 is transmitted to a dental laser irradiation handpiece 2, to be mentioned later, via a laser transmitter 11a. The laser treatment apparatus 1 has a flexible hose 3 feeding laser beam from the laser oscillator 11, water from the water delivery circuit 12 and air from the air delivery circuit 13, which are supplied by the apparatus body 10, to the dental laser irradiation handpiece 2 outside the apparatus body 10, a setting/operating portion 14 and a display 15 provided on the upper front face of the apparatus body 10, and a foot controller 16 connected with the laser apparatus body 10. The flexible hose 3 includes bundles of a laser beam guide body 11b connected with the laser transmitter 11a of the laser oscillator 11, a water supply tube 12a connected with the water delivery circuit 12, and an air supply tube 13a connected with the air delivery circuit 13 and is connected with a base portion of the dental laser irradiation handpiece 2. The setting/operating portion 14 comprises an operation key, a touch panel, a rotary knob and the like in such a manner that irradiation conditions of laser beam, spray amount of water or air, existence of spraying, and the like are able to be set or operated. The display 15 comprises a liquid crystal panel (LCD) and the like and displays the set irradiation conditions and the like. The foot controller 16 is a switch for operating irradiation of laser beam or for operating supply of water or air and is operated with an operator's foot. Furthermore, the laser apparatus body 10 includes a cooling device for the laser oscillator attached to the laser oscillator 11 and an electric supply (they are not shown in the figure).

The water delivery circuit 12 has a tank for containing water such as purified water or normal saline and supplies water to the water supply tube 12a by means of a pump mechanism. The air delivery circuit 13 is designed to generate compressed air or compressed inert gas to be supplied to the air supply tube 13a. A blower or a compressor is used for generating air, and a gas cylinder filled with compressed inert gas is used for generating inert gas.

Laser generated by the laser oscillator 11 is therapeutic laser with high absorbability in water such as Er-YAG laser, $CO_2$ laser, Er,Cr:YSGG laser, and Ho:YAG laser. Laser beam generated by the laser oscillator 11 is guided to the dental laser irradiation handpiece 2 via the laser transmitter 11a and the light guide body 11b. The light guide body 11b can be a solid or hollow optical fiber (waveguide) housed in the flexible hose 3. Manipulator-type transmitter (multiple joint transmitter) can be used other than the flexible hose 3.

The dental laser irradiation handpiece 2 of the embodiment of the present invention comprises a connection base portion 20A connecting with the flexible hose 3, a grip portion (a barrel portion) 20B connected with the connection base portion 20A to be grasped and handled by an operator's hands, a handpiece main body 20 including a head portion 20C extending from the tip side of the grip portion 20B, and a dental laser irradiation tip 4 to be detachably mounted on the head portion 20C. A connection portion of the flexible hose 3 and the connection base portion 20A of the handpiece body 20 is constituted with a detachable connector portion. In such connection, the laser beam guide body 11b, the water supply tube 12a and the air supply tube 13a in the flexible hose 3 are connected with base end portions of a laser beam guide path 21, a water pipe line 22, and an air pipe line 23, to be mentioned later, respectively, in the handpiece body 20. As a result, the laser beam guide body 11b in the flexible hose 3 is optically connected with the laser beam guide path 21 in the handpiece body 20, the water supply tube 12a in the flexible tube 3 is water-tightly connected with the water pipe line 22 in the handpiece body 20, and the air supply tube 13a in the flexible hose 3 is air-tightly connected with the air pipe line 23 in the handpiece body 20.

Figure 2:
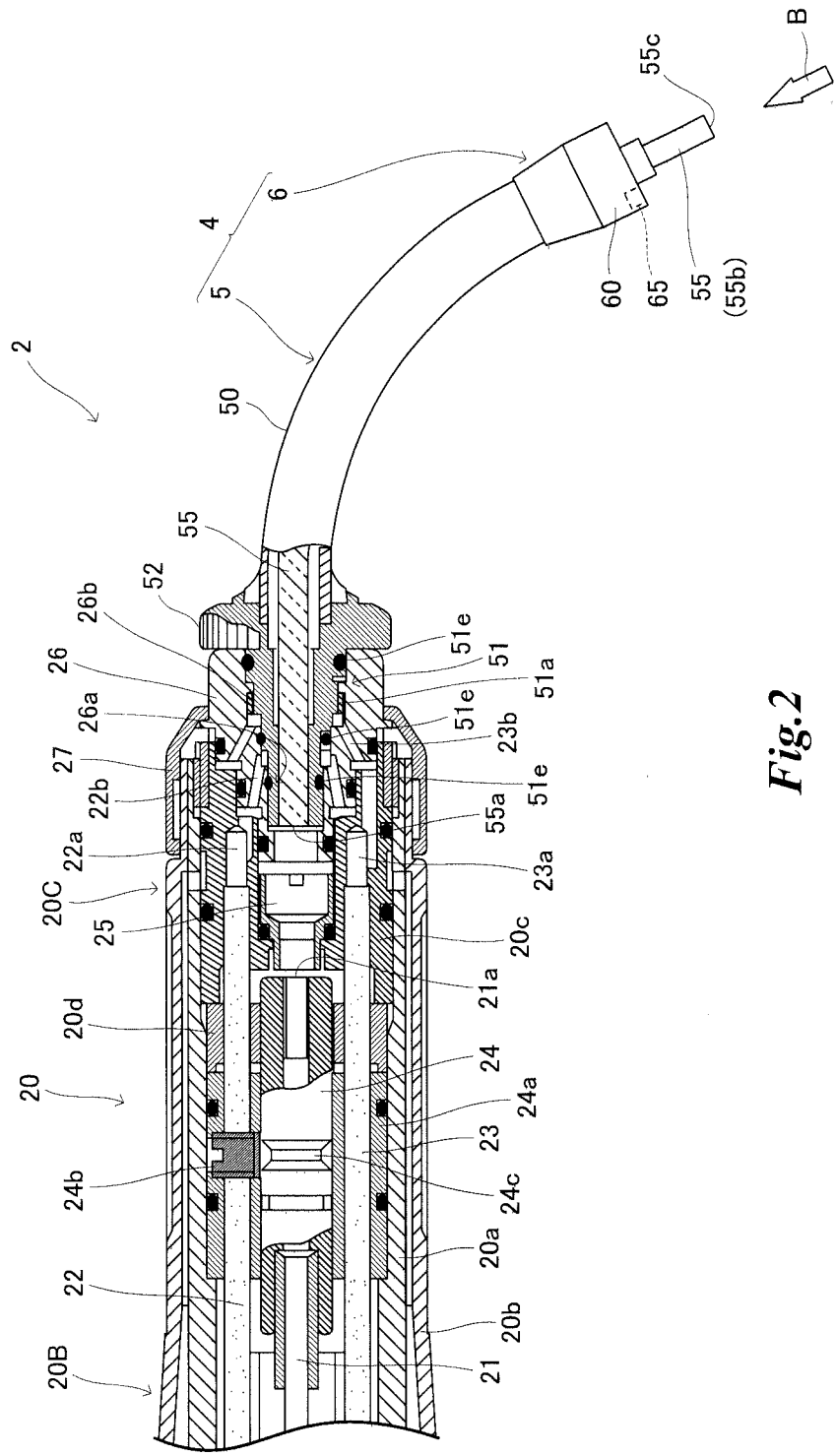
FIG. 2 is a partially broken enlarged view of the part "A" in FIG. 1.
Figure 3:
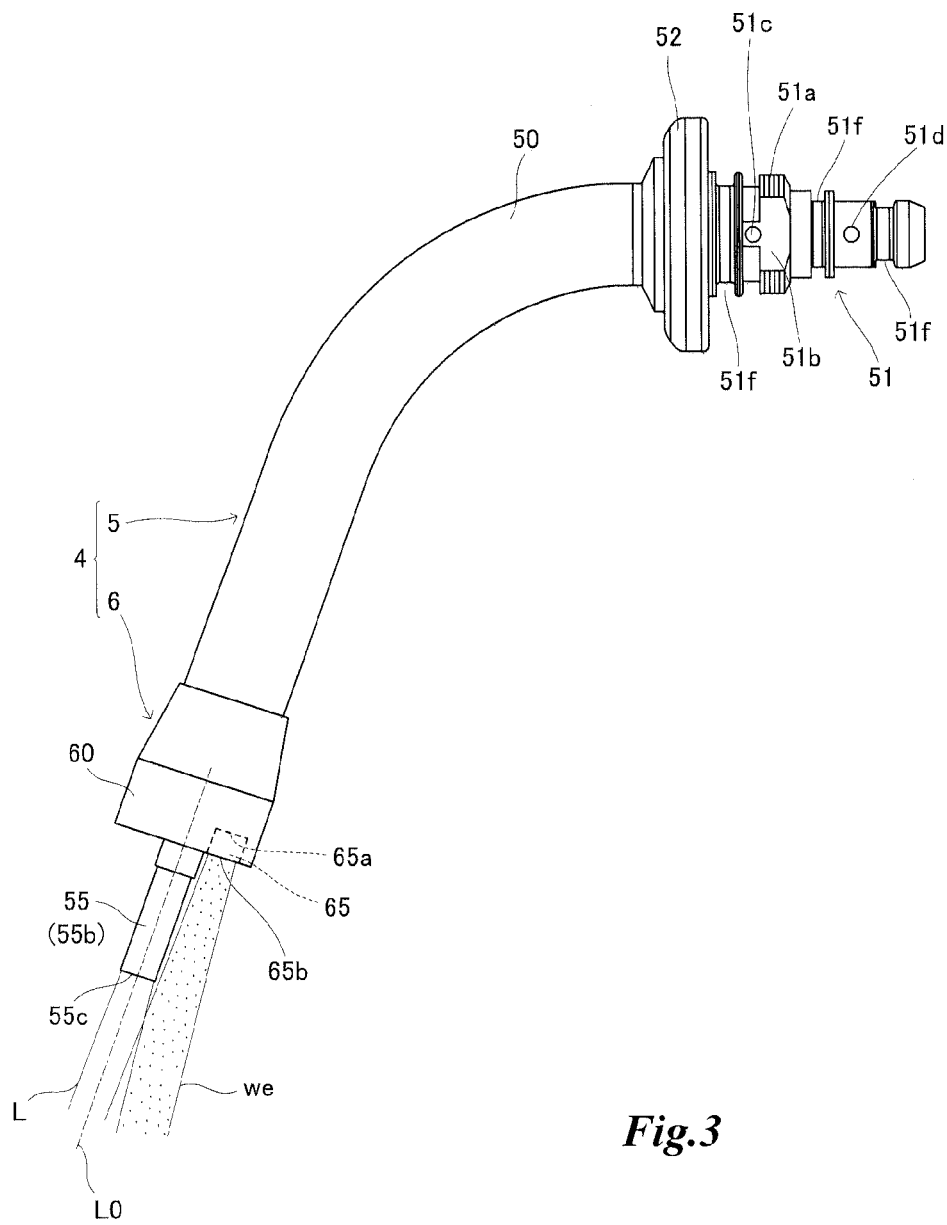
FIG. 3 is a front view of the laser irradiation tip to be mounted on the dental laser irradiation handpiece of the dental laser treatment apparatus.

The connection portion of the handpiece body 20 and the dental laser irradiation tip 4 is explained in detail referring to FIG. 2 and FIG. 3. As shown in FIG. 2, the handpiece body 20 has a cylindrical main tube 20a extending from the grip portion 20B to the head portion 20C and an exterior sleeve portion 20b externally fitted on the cylindrical main tube 20a. The laser beam guide path 21 is constituted with a hollow or solid waveguide (optical fiber) and is concentrically provided in the handpiece body 20 along the longitudinal direction. The tip end portion of the laser beam guide path 21 is held with a ferrule 24 as far as the inside of the head portion 20C. The ferrule 24 is inserted into a support ring 24a concentrically fitted in the main tube 20a to be supported, the tip end of a fixing threaded member 24b screwed to the support ring 24a is aligned with a circumferential groove 24c formed around the ferrule 24, thereby positioning the ferrule 24 to be fixed relative to the support ring 24a. The support ring 24a is positioned at a predetermined position in the main tube 20a to be internally fitted and supported via a spacer collar member 20d by means of a tubular holder member 20c screwed in the tip end portion of the main tube 20a. A tip end 21a of the laser beam guide path 21 inserted to the ferrule 24 to be supported faces an optical collecting lens (drum lens) 25 held by the holder member 20c.

The water pipe line 22 and the air pipe line 23 are formed with a narrow tube; the tip end portions are held by the holder member 20c and are communicated with a water communication pipe line 22a and an air communication pipe line 23a provided for the holder member 20c, respectively. A tip holder 26 is fitted to the holder member 20c and is fixed and held in a fitted condition when a hexagon cap nut 27 is screwed to a tip end portion of the exterior sleeve portion 20b. The tip holder 26 is a hollow tubular body and a concentrically formed inner tubular portion 26a is a joint portion for detachably screwing a tip main body 5 constituting the dental laser irradiation tip 4 to be mentioned later. A water communication line 22b and an air communication line 23b are formed on a tube wall of the tip holder 26. When the tip holder 26 is fitted and fixed to the holder member 20c, the water communication line 22b and the air communication line 23b are connected with the water communication pipe line 22a and the air communication pipe line 23a via the circumferential grooves formed on the periphery of the tip holder 26, respectively. The tip end portions of the communication lines 22b, 23b are opened toward the inner tubular portion 26a of the tip holder 26. Female threaded portion 26b for screwing and connecting with the tip main body 5 is formed on the inner tubular portion 26a of the tip holder 26.

In FIG. 2, the water pipe line 22 and the air pipe line 23, the water communication pipe line 22a and the air communication pipe line 23a, the water communication line 22b and the air communication line 23b, the fixing threaded member 24b and so on are shown on the same section for convenience; however, they should be formed at appropriate places in the circumferential direction in view of design in such a manner that they do not interfere each other. The air communication pipe line 23a may be designed to be diverged for introducing cooling air around the optical collecting lens 25 and the tip end 21a of the laser beam guide path 21 in order to cool down the vicinity therearound and to remove foreign matters attached on the tip end 21a of the laser beam guide path 21, an incidence plane and an output plane of the optical collecting lens 25, or a base end surface 55a of the optical fiber 55 to be mentioned later. If the laser beam guide path 21 in the handpiece body 20 is hollow, the optical collecting lens 25 is able to be cooled down or foreign matters in the optical fiber 55 are able to be removed by introducing air in the laser beam guide path 21.

A plug portion 51 in the form of bamboo shoot, multistep like portion, to be screwed and connected with the inner tubular portion 26a of the tip holder 26 and a knurled rotary knob 52 for screwing the plug portion 51 are integrally formed at a connection portion of the main body 5 with the head portion 20C of the handpiece main body 20. A male threaded portion 51a to be screwed to the female threaded portion 26b is provided on the circumference of the plug portion 51 and a milled surface 51b is formed on a part of the male threaded portion 51a. A gap is formed between the male threaded portion 51a and the female threaded portion 26b, which are screwed together, by providing the milled surface 51b and is provided with an air inlet 51c. When the plug portion 51 is screwed and connected with the tip holder 26, the air inlet 51c is designed to be aligned with the air communication line 23b and to be communicated with an air flow path 54 (referring to FIG. 5) in an exterior pipe 50, to be mentioned later, via the plug portion 51. A water inlet 51d is formed at a region of the circumference of the plug portion 51 in the axially opposite direction to the air inlet 51c. When the plug portion 51 is screwed and connected with the tip holder 26, the water inlet 51d is designed to be aligned with the water communication line 22b and to be communicated with a water flow path 53 (referring to FIG. 5) to be mentioned later, in the exterior pipe 50 via the plug portion 51. Three O-rings 51e . . . (referring to FIG. 2) for isolating air communication regions and water communication regions are provided for the circumference of the plug portion 51 via O-ring grooves 51f . . . (referring to FIG. 3) in such a manner that air communication via the air inlet 51c becomes air-tight and water communication via the water inlet 51d becomes water-tight. The base end surface 55a of the optical fiber 55 faces a light emitting surface of the collecting lens 25 to execute optical connection of laser beam via the collecting lens 25.

Figure 4:
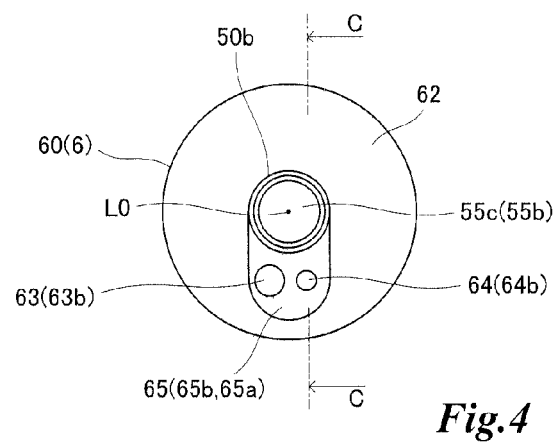
FIG. 4 is an enlarged view seen from the arrow "B" in FIG. 2.
Figure 5:
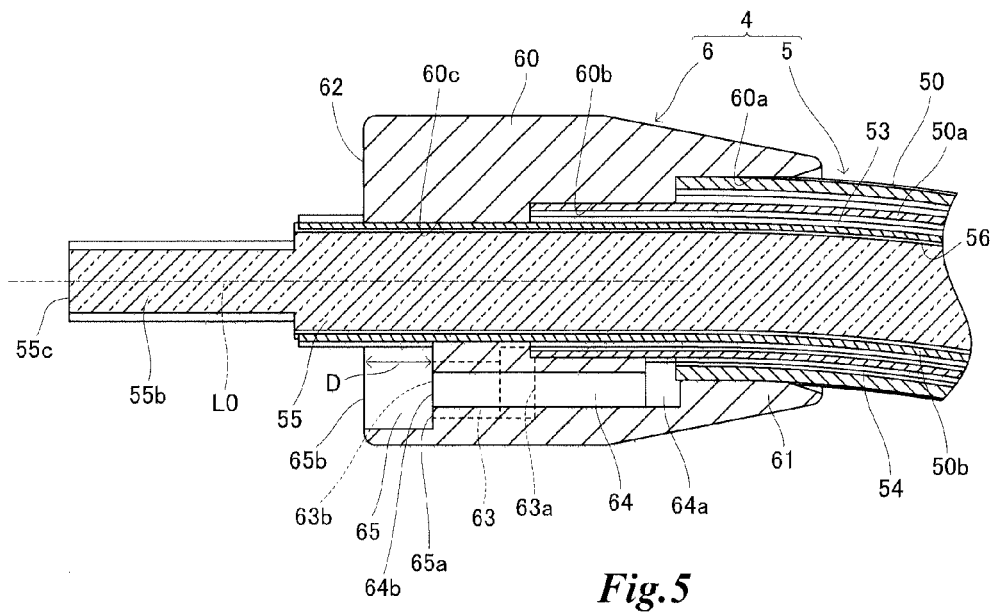
FIG. 5 is a fragmentary enlarged sectional view along the line C-C in FIG. 4.

The laser irradiation tip 4 of the embodiment of the present invention is explained in detail referring to FIG. 4 and FIG. 5. The laser irradiation tip 4 comprises the tip main body 5 made of a curved bar-shaped body and a laser irradiation tip end member (the tip end portion of the tip) 6 detachably mounted on a tip end portion of the main body 5. The tip main body 5 has the curved exterior pipe 50, an intermediate pipe 50a coaxially provided in the exterior pipe 50, and an inner pipe 50b coaxially provided in the intermediate pipe 50a. The tip side of the pipe 50a extends so as to project from a tip end of the intermediate pipe 50a and a tip side of the inner pipe 50b extends so as to project from a tip end of the intermediate pipe 50a. The plug portion 51 and the knurled rotary knob 52 are integrally formed with the exterior pipe 50. An annular gap between the exterior pipe 50 and the intermediate pipe 50a constitutes the air flow path 54, an annular gap between the intermediate pipe 50a and the inner pipe 50b constitutes the water flow path 53, and an inner tubular portion of the inner pipe 50b constitutes a fiber guide portion 56. The optical fiber 55, the water flow path 53 and the air flow path 54, which are inserted into the fiber guide portion 56, are coaxially formed and are provided substantially in parallel with the tip main body 5. The plug portion 51 and the knurled rotary knob 52 of the tip main body 5 are integrally formed with metal (stainless steel, nickel-plated brass or the like) or resin. The exterior pipe 50 is made of metal (stainless steel, brass or the like), ceramics, resin or the like and has an outside diameter of 1.0 to 3.0 mm. The material and dimension are optionally selected and designed in view of material and dimension of surrounding members and necessity of sterilization at high temperature. In view of application to a tip mounted to a contra-type handpiece, the outside diameter of the external pipe 50 is able to be larger than 3.0 mm.

The laser irradiation tip end member (the tip end portion of the laser irradiation tip) 6 is detachably mounted on the tip end portion of the tip main body 5. The laser irradiation tip end member 6 in the figures, which is hollow and in the form of an approximate cylinder, is formed with a molded body 60 made of resin or the like and has a mounting portion (connection portion) 61 detachable to the exterior pipe 50 of the tip main body 5 by external press-fit. An inner tubular portion of the molded body 60 comprises a large-diameter inner tubular portion 60a of which inside diameter is approximately equal to or a little smaller than the outside diameter of the exterior pipe 50, a middle-diameter inner tubular portion 60b of which inside diameter is approximately equal to the outside diameter of the intermediate pipe 50a, and a small-diameter inner tubular portion 60c of which inside diameter is approximately equal to the outside diameter of the inner pipe 50. The large-diameter inner tubular portion 60a, the middle-diameter inner tubular portion 60b and the small-diameter tubular portion 60c are formed in concentric with an axial center Lo of the molded body 60 and in a stepped manner from the mounting portion 61 to a front end surface 62. When the laser irradiation tip end member 6 is mounted on the tip main body 5, the large-diameter inner tubular portion 60a is fitted under pressure onto the exterior pipe 50, the middle-diameter inner tubular portion 60b is air-tightly fitted onto the intermediate pipe 50a, and the small-diameter inner tubular portion 60c is water-tightly fitted onto the inner pipe 50b. A part of the molded body 60 corresponding to the large-diameter inner tubular portion 60a substantially constitutes the mounting portion 61.

When the laser irradiation tip end member 6 is mounted on the tip main body 5, the inner pipe 50b of the tip main body 5 is fitted to the small-diameter inner tubular portion 60c, and extends so as to penetrate the laser irradiation tip end member 6, namely the molded body 60, along the axial center Lo and to project out of the front end surface 62. The fiber guide portion 56 formed by the inner tubular portion of the inner pipe 50b reaches the laser irradiation tip end member 6 and also constitutes the fiber guide portion of the laser irradiation tip end member 6. The optical fiber 55 to be inserted in the fiber guide portion 56 further projects from the tip end of the fiber guide portion 56. An exterior body, called a jacket, of a projecting portion of the optical fiber 55 is removed so as to expose a core material 55b made of a core and a clad, or solely of a core, and the optical fiber 55 is concentrically held with the laser irradiation tip end member 6. The tip end surface 55c of the core material 55b constitutes an output end of laser beam.

A stepped portion of the small-diameter inner tubular portion 60c and the middle-diameter inner tubular portion 60b of the molded body 60 is formed with a water pocket 63a communicated with the water flow path 53 and a water guide path 63 is formed in parallel with the axial center Lo from the water pocket 63a to the front end surface 62. A stepped portion of the middle-diameter inner tubular portion 60b and the large-diameter inner tubular portion 60a is formed with an air pocket 64a communicated with the air flow path 54 and an air guide path 64 extending in parallel with the axial center Lo from the air pocket 64a to the front end surface 62 is formed in the proximity of the water guide path 63. The molded body 60 has a concave portion 65 which opens on the front end surface 62 and dents toward the tip main body 5. Tip end open portions 63b, 64b of the water guide path 63 and the air guide path 64 face a bottom portion 65a of the concave portion 65. The open portion of the concave portion 65 constitutes a spray end 65b, to be mentioned later, of mixed water/air mist, and depth "D" of the concave portion 65 from the spray end 65b is 0.5 to 1.5 mm. Such the concave portion 65 constitutes a mixing chamber of water and air (allotted with numeral 65, hereinafter). If the depth "D" becomes larger than 1.5 mm by increasing air pressure, it is possible to spray appropriate mist although there causes a little disturbance.

The sectional area of the concave portion 65 (dimension of surface area orthogonal to the axial center Lo) is designed to be larger than the total dimension of the tip end open portions 63b, 64b of the water guide path 63 and the air guide path 64. Specifically, dimension of the tip end open portion 63b of the water guide path 63 is designed to be 0.0079 to 3.14 square millimeter (0.1 to 2 mm in diameter) and dimension of the tip end open portion 64b of the air guide path 64 is designed to be 0.0079 to 3.14 square millimeter (0.1 to 2 mm in diameter). In the figure, dimension of the tip end open portion 63b of the water guide path 63 is larger than dimension of the tip end open portion 64b of the air guide path 64; however, they can be same or vice-versa. The open dimension of the spray end 65b (sectional area of the concave portion 65) is designed to be 0.35 to 20 square millimeter.

How to cut and remove caries and so on of teeth using the above-mentioned dental laser treatment apparatus 1 is briefly explained. The water delivery circuit 12 and the air delivery circuit 13 are controlled by the setting/operating portion 14 of the laser apparatus body 10 in such a manner that water amount flowing in the water guide path 63 becomes 1.0 to 20.0 milliliter per minute and air amount flowing in the air guide path 64 becomes 0.5 to 15.0 litter per minute. Laser output of the laser oscillator 11 is controlled to cut and remove appropriately. An operator grasps the grip portion 20B of the laser irradiation handpiece 2 with his hand, inserts the laser irradiation tip 4 to a patient's oral cavity (not shown), and puts the tip end surface 55c of the optical fiber 55 close to the surface of a tooth to be treated (not shown). The tip main body 5 of the laser irradiation tip 4 is formed with a curved slim bar-shaped body, so that the operator's eyesight is not obstructed and the objective tooth is easily accessed. The operator operates the foot controller 16 with his foot or presses several switches (not shown) provided for the laser irradiation handpiece 2 with his finger, and irradiates laser beam from the output end to an objective tooth. Simultaneously, the water delivery circuit 12 and the air delivery circuit 13 are driven to flow water and air to the water-air mixing chamber 65 through the water guide path 63 and the air guide path 64, water and air are mixed in the mixing chamber 65, then the mixed water/air mist is sprayed in parallel with the irradiation direction of laser light.

The sectional area of the water-air mixing chamber (concave portion) 65 is designed to be larger than the total area of open dimension of the tip end open portions 63b, 64b, so that flow pressure values of water and air flown in the water-air mixing chamber 65 are reduced and water is refined by the action of air while passing through the mixing chamber 65, thereby generating uniformly mixed water/air mist of minute water particles. The mixed water/air mist is sprayed from the spray end 65b in a spray pattern "we" shown in FIG. 3. The spray pattern "we" comprises uniform mist of minute water particles and is approximately parallel with an irradiation pattern "L" of laser beam irradiated from the tip end surface 55c of the optical fiber 55, thereby avoiding absorption of laser beam in the mixed water/air mist before the laser beam reaches the objective tooth. As a result, cutting efficiency is improved and laser output is efficiently reduced.

Figure 6:
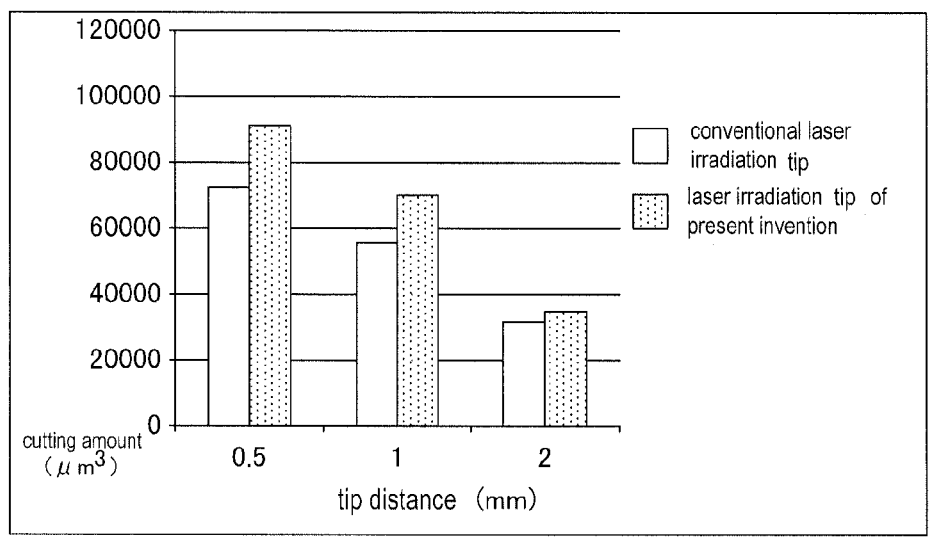
FIG. 6 shows a bar chart showing the relation of cutting amount and the distance between the tip end of the laser irradiation tip and the object to be irradiated when the surface of the object to be irradiated is cut with the laser irradiation tip of the present invention, compared with the conventional laser irradiation tip.

FIG. 6 is a graph of validation results showing relation of cutting amount by laser irradiation and distance (tip end distance) between the tip end of the tip and the surface of the body to be irradiated when laser is irradiated while spraying mixed water/air mist to a pseudo tooth (object to be irradiated). The outlined bar graph shows the case when a conventional laser irradiation tip without having the mixing chamber of water and air of the present invention is used and the dotted bar graph shows the case when the laser irradiation tip of the present invention is used. In both cases, laser type, laser output, and flow amount of water or air are the same, the tip end distance is changed to 0.5 mm, 1.0 mm, and 2.0 mm, and cutting amount in volume is measured after being irradiated for the predetermined time. Measurement is executed five times per tip end distance and the average value is shown.

It is found in FIG. 6 that cutting ability of the laser irradiation tip of the present invention is improved by 1.2 times, compared with the conventional tip at the distance of 0.5 mm and 1.0 mm from the tip end of the tip to the object to be irradiated. It means that laser is avoided from being absorbed in the mixed water/air mist before reaching the object to be irradiated. In the validation test, it is found that mixed water/air mist adheres to the surface of the object to be irradiated and forms a thin water layer when the laser irradiation tip of the present invention is used. It is confirmed that such validation results support the laser energy is absorbed and distributed, and efficient evaporation (cutting) is executed. In addition, sprayed mixed water/air mist does not form a water drop on the surface of the object to be irradiated, so that it is not necessary to suck and remove the water drop.

In the above-mentioned embodiment, the dental laser irradiation apparatus is exemplified; however, the present invention is not limited to such an apparatus, and the present invention is able to be used for other laser treatment apparatus. One water-air mixing chamber 65 is used for the laser irradiation tip 4 in the embodiment; however, a plurality of mixing chambers can be provided around the axial center Lo of the optical fiber. The shape of the water-air mixing chamber 65 (shape seen from the direction of the arrow "B" in FIG. 2) is not limited to that shown in the figure; it can be circular, rectangular, oval or the like. The laser irradiation tip end member 6 is detachably mounted to the tip main body 5 by compression; however, it can be mounted with a screw. The laser irradiation tip end member 6 detachably inserted by compression is advantageous for applying to an existing laser irradiation tip. Furthermore, in place of the detachable laser irradiation tip end member 6, a part of the laser irradiation tip can be constituted in such a manner that the tip end portion of the tip is adhered to be integrated by adhesive agent to the exterior pipe 50 constituting the tip main body 5 or is integrally formed with the exterior pipe 50.

REFERENCE SIGNS LIST 1 laser treatment apparatus
11 laser oscillator
11a laser transmitter
12 water delivery circuit
13 air delivery circuit
2 laser irradiation handpiece
21 laser beam guide path
22 water pipe line
23 air pipe line
4 laser irradiation tip
5 tip main body
6 laser irradiation tip end member (tip end portion)
53 water flow path
54 air flow path
55 optical fiber
56 fiber guide portion
61 mounting portion (connection portion)
62 front end surface
63 water guide path
63a tip end open portion
64 air guide path
64a tip end open portion
65 water-air mixing chamber (concave portion)
65a bottom portion
65b spray end

The invention claimed is:
1. A laser irradiation tip comprising:
a main body connected with a handpiece, wherein the main body irradiates therapeutic laser with absorbability in water, and
a tip end portion connected with said main body,
wherein said main body of said laser irradiation tip comprises:
an optical fiber that guides said therapeutic laser,
a water flow path, and
an air flow path,
said optical fiber, said water flow path, and said air flow path being coaxially arranged in said main body,
wherein said tip end portion of said laser irradiation tip comprises:
a connection portion that connects with said main body,
a water guide path that communicates with said water flow path of said main body,
an air guide path that communicates with said air flow path of said main body, a fiber guide portion that inserts a tip side portion of said optical fiber so as to project from a front end surface of said tip end portion, and a mixing chamber of water and air having a concaved form such that the mixing chamber opens on said front end surface of said tip end portion and dents toward a main body side of said laser irradiation tip, wherein openings of said water guide path and said air guide path are arranged at a bottom of said concaved form of said mixing chamber, and wherein said mixing chamber is configured to mix water from said water guide path and air from said air guide path and spray mixed mist of water and air substantially parallel to said therapeutic laser in an irradiation direction of said therapeutic laser from a spray end at an opening of said mixing chamber.

2. The laser irradiation tip as set forth in claim 1, wherein said main body of said laser irradiation tip is constituted with a curved bar-shaped body.

3. A laser irradiation handpiece,
wherein a handpiece body capable of handling with fingers incorporates a laser beam guide path for guiding therapeutic laser with high absorbability in water, a water pipe line, and an air pipe line; and wherein said laser irradiation tip as set forth in claim 2 is attached to said handpiece body in such a manner that said optical fiber provided for said laser irradiation tip, said water flow path, and said air flow path are connected with said laser beam guide path, said water pipe line, and said air pipe line, respectively.

4. The laser irradiation tip as set forth in claim 1, wherein amount of water flowing in said water guide path is 1.0 to 20.0 milliliter per minute and amount of air flowing in said air guide path is 0.5 to 15.0 liter per minute.

5. A laser irradiation handpiece,
wherein a handpiece body capable of handling with fingers incorporates a laser beam guide path for guiding therapeutic laser with high absorbability in water, a water pipe line, and an air pipe line; and wherein said laser irradiation tip as set forth in claim 4 is attached to said handpiece body in such a manner that said optical fiber provided for said laser irradiation tip, said water flow path, and said air flow path are connected with said laser beam guide path, said water pipe line, and said air pipe line, respectively.

6. The laser irradiation tip as set forth in claim 1, wherein depth of said concave portion from said spray end is 0.5 to 1.5 mm.

7. A laser irradiation handpiece,
wherein a handpiece body capable of handling with fingers incorporates a laser beam guide path for guiding therapeutic laser with high absorbability in water, a water pipe line, and an air pipe line; and wherein said laser irradiation tip as set forth in claim 6 is attached to said handpiece body in such a manner that said optical fiber provided for said laser irradiation tip, said water flow path, and said air flow path are connected with said laser beam guide path, said water pipe line, and said air pipe line, respectively.

8. The laser irradiation tip as set forth in claim 1,
wherein said tip end portion of said laser irradiation tip is another member different from said main body of said laser irradiation tip, and wherein said connection portion is a mounting portion capable of attaching or removing said tip end portion to or from said main body.

9. A laser irradiation handpiece,
wherein a handpiece body capable of handling with fingers incorporates a laser beam guide path for guiding therapeutic laser with high absorbability in water, a water pipe line, and an air pipe line; and wherein said laser irradiation tip as set forth in claim 8 is attached to said handpiece body in such a manner that said optical fiber provided for said laser irradiation tip, said water flow path, and said air flow path are connected with said laser beam guide path, said water pipe line, and said air pipe line, respectively.

10. A laser irradiation handpiece,
wherein a handpiece body capable of handling with fingers incorporates a laser beam guide path for guiding therapeutic laser with high absorbability in water, a water pipe line, and an air pipe line; and wherein said laser irradiation tip as set forth in claim 1 is attached to said handpiece body in such a manner that said optical fiber provided for said laser irradiation tip, said water flow path, and said air flow path are connected with said laser beam guide path, said water pipe line, and said air pipe line, respectively.

11. A laser treatment apparatus comprising:
a laser oscillator for oscillating therapeutic laser with high absorbability in water;
a laser transmitter for transmitting said therapeutic laser;
a water delivery circuit;
an air delivery circuit; and
said laser irradiation handpiece as set forth in claim 10.

12. A laser irradiation tip end member comprising:
a mounting portion capable of being attached to or removed from a main body of a laser irradiation tip, wherein said main body comprises:
an optical fiber that guides therapeutic laser with absorbability in water,
a water flow path, and
an air flow path,
said optical fiber, said water flow path, and said air flow path being coaxially arranged in said main body;
a water guide path that communicates with said water flow path;
an air guide path that communicates with said air flow path;
a fiber guide portion that inserts a tip side portion of said optical fiber so as to project from a front end surface of a tip end portion of said laser irradiation tip; and
a mixing chamber of water and air having a concaved form such that the mixing chamber opens on said front end surface of said tip end portion and dents toward a main body side of said laser irradiation tip,
wherein openings of said water guide path and said air guide path are arranged at a bottom of said concaved form of said mixing chamber, and
wherein said mixing chamber is configured to mix water from said water guide path and air from said air guide path and spray mixed mist of water and air substantially parallel to said therapeutic laser in an irradiation direction of said therapeutic laser from a spray end at said opening of said mixing chamber.

* * * * *